United States Patent

Hermecz et al.

[11] Patent Number: 5,091,530
[45] Date of Patent: Feb. 25, 1992

[54] BARON CHELATES OF QUINOLINE CARBOXYLIC ACIDS

[75] Inventors: István Hermecz; Géza Kereszturi; Lelle Vasvári; Ágnes Horváth, all of Budapest; Márie Balogh, Dunakeszi; Péter Ritli, Budapest; Judit Sipos, Budapest; Anikó Pajor, Budapest; Katalin Mármarosi, Biatorbágy, all of Hungary

[73] Assignee: Chinoin Gyogyszer- es Vegyeszeti Termekek Gyara Rt., Budapest, Hungary

[21] Appl. No.: 290,105

[22] PCT Filed: Apr. 8, 1988

[86] PCT No.: PCT/HU88/00019
§ 371 Date: Nov. 23, 1988
§ 102(e) Date: Nov. 23, 1988

[87] PCT Pub. No.: WO88/07993
PCT Pub. Date: Oct. 20, 1988

[30] Foreign Application Priority Data
Apr. 8, 1987 [HU] Hungary ............... 1505/87
Feb. 26, 1988 [HU] Hungary ............... 1505/87

[51] Int. Cl.⁵ .................................. C07D 403/04
[52] U.S. Cl. ........................ 544/229; 544/363; 546/13; 546/156
[58] Field of Search ........... 544/229, 363; 546/13

[56] References Cited

U.S. PATENT DOCUMENTS

| | | | |
|---|---|---|---|
| 4,670,444 | 6/1987 | Grohe et al. ............ | 544/363 |
| 4,806,645 | 2/1989 | Hermecz et al. .......... | 546/13 |
| 4,871,849 | 10/1989 | Hermecz et al. ......... | 544/229 |
| 4,940,794 | 7/1990 | Hermecz et al. ......... | 546/13 |

FOREIGN PATENT DOCUMENTS

| | | | |
|---|---|---|---|
| 59-80683 | 5/1984 | Japan ................. | 544/229 |
| 57-233684 | 7/1984 | Japan . | |
| 60-78986 | 5/1985 | Japan . | |
| 64-19069 | 1/1989 | Japan ................. | 544/363 |
| WO87/03594 | 6/1987 | PCT Int'l Appl. ........ | 546/13 |
| WO87/03595 | 6/1987 | PCT Int'l Appl. ........ | 546/13 |
| WO88/07993 | 10/1988 | PCT Int'l Appl. ........ | 544/363 |
| WO88/07998 | 10/1988 | PCT Int'l Appl. ........ | 546/13 |
| WO88/10253 | 12/1988 | PCT Int'l Appl. ........ | 544/363 |

Primary Examiner—C. Warren Ivy
Assistant Examiner—James H. Turnipseed
Attorney, Agent, or Firm—Herbert Dubno; Andrew Wilford; Jonathan Myers

[57] ABSTRACT

The invention relates to a new process for the preparation of compounds of the general Formula I

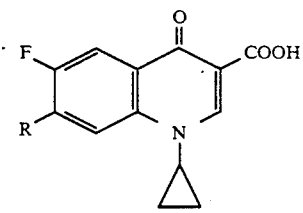

/wherein R stands for piperazinyl, 4-methyl-piperazinyl or 4-ethyl-piperazinyl group/ and pharmaceutically acceptable salts thereof which comprises reacting a compound of the general Formula II

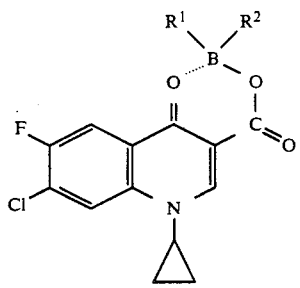

/wherein $R^1$ and $R^2$ stand for halogen, for an aliphatic acyloxy group containing 2 to 6 carbon atoms and optionally substituted by halogen, or for an aromatic acyloxy group containing 7 to 11 carbon atoms/ with a piperazine derivative of the general Formula

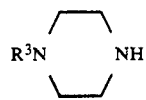

/wherein $R^3$ stands for hydrogen, methyl or ethyl/ or a salt thereof and subjecting the compound of the general Formula IV (Abstract continued on next page.)

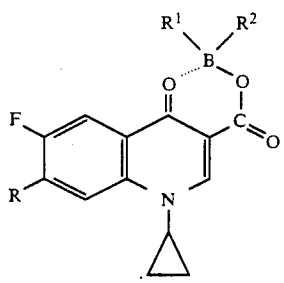

thus obtained /wherein R, $R^1$ and $R^2$ are as stated above/ to hydrolysis after or without isolation and if desired converting the compound of the general Formula I thus obtained into a salt thereof or setting free the same from its salt.

The compounds of the general Formula I are known antibacterial agents.

The advantage of the present invention is that it makes the desired compounds of the general Formula I available in a simple manner, with high yields and in a short reaction time.

3 Claims, No Drawings

BARON CHELATES OF QUINOLINE CARBOXYLIC ACIDS

CROSS REFERENCE TO RELATED APPLICATIONS

This application is national phase of PCT/HU88/00019, filed 8 April 1988 and based upon Hungarian national application 1505/89 filed 8 April 1987 under the International application.

FIELD OF THE INVENTION

This invention relates to a new process for the preparation of 1-cyclopropyl-7-substituted-6-fluoro-4-oxo-1,4-dihydro-quinoline-3-carboxylic acid derivatives and pharmaceutically acceptable salts thereof.

BACKGROUND OF THE INVENTION

It is known that the 1-cyclopropyl-7-substituted-6-fluoro-4-oxo-1,4-dihydro-quinoline-3-carboxylic acid derivatives of the Formula (I)

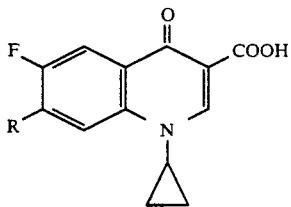

wherein R stands for a piperazinyl, 4-methyl-piperazinyl or 4-ethyl-piperazinyl group possess high antibacterial activity (Eur. J. Clin. Microbiol. 1983, 2, page 111; J. Clin. Pharmacol. 1985, 25, page 82; Drugs Exptl. Clin. Res. 1985, 5, page 317).

The quinoline carboxylic acids of the Formula I can be prepared by reacting 1-cyclopropyl-6-fluoro-4-oxo-1,4-dihydro-quinoline-3-carboxylic acid and a cyclic amine in the presence of a solvent at a temperature of 135°–140° C. for 2 hours (German open application 3,033,157; German open application 3,142,854.

DESCRIPTION OF THE INVENTION

According to the present invention there is provided a new process for the preparation of 1-cyclopropyl-7-substituted-6-fluoro-4-oxo-1,4-dihydro-quinoline-3-carboxylic acid derivatives of the Formula I, wherein R has the same meaning as stated above, which comprises reacting a compound of the Formula II

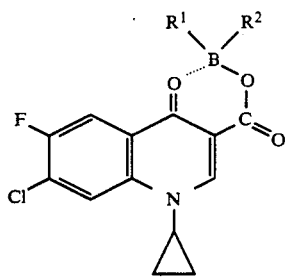

wherein $R^1$ and $R^2$ are the same or different and stand for halogen, for an aliphatic acyloxy group containing 2 to 6 carbon atoms optionally substituted by halogen, or for an aromatic acyloxy group containing 7 to 11 carbon atoms, with a cyclic amine of the Formula

wherein $R^3$ stands for hydrogen, methyl or ethyl or a salt thereof and subjecting the compound of the Formula IV

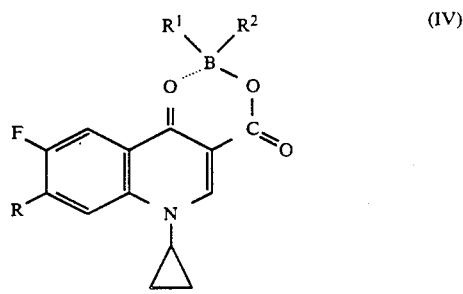

thus obtained to hydrolysis.

The advantage of the process of the present invention is that it makes the desired compound of the Formula I available in a simple manner with high yields and in a short reaction time.

According to a preferred form of embodiment of the process of the present invention the borate derivative of the Formula IV, wherein R, $R^1$ and $R^2$ are as stated above, is converted into the desired quinoline-3-carboxylic acid of the Formula I without isolation.

The borate derivatives of the Formula IV are new compounds.

The borate derivatives of the Formula II and the cyclic amine of the general Formula III can be reacted optionally in the presence of an inert organic solvent and an acid binding agent.

As inert organic solvents preferably acid amides (e.g. dimethyl formamide, dimethyl acetamide), ketones (e.g. acetone, methyl ethyl ketone), ethers (e.g. dioxane, tetrahydrofuran, diethyl ether), esters (e.g. ethyl acetate, methyl acetate, ethyl propionate), sulfoxides (e.g. dimethyl sulfoxide or alcohols e.g. methanol, ethanol, 1-decanol, butanol) may be used.

As acid binding agent an organic or inorganic base may be used. From the group of organic bases trialkyl amines (e.g. triethyl amine, tributyl amine), cyclic amines (e.g. pyridine, 1,5-diazabicyclo[5,4,0]undec-5-ene, 1,5-diazabicyclo[4,3,0]non-5-ene, 1,4-diazabicyclo-[2,2,2]octane) can be mentioned, while as inorganic base preferably hydroxides or carbonates of alkali or alkaline earth metals can be used. Thus as acid binding agent preferably potassium carbonate, potassium hydrogen carbonate, sodium hydroxide, calcium hydroxide, etc. or an excess of the amine of the Formula III can be used.

The boron derivative of the Formula II and the cyclic amine of the Formula III can be reacted at a temperature ranging from 0° to 200° C., depending on the solvent used. The reaction time may vary between half an hour and 10 hours depending on the reaction temperature. If the reaction is carried out at an elevated temperature, the reaction time can be shortened. The above reaction conditions are but preferable values and other conditions may be used as well.

The borates of the Formula IV (wherein R, $R^1$ and $R^2$ are as stated above) can be hydrolysed to the desired quinoline-3-carboxylic acids of the Formula I, after or without isolation, under acidic or basic conditions. The compound of the Formula IV (wherein R is as stated above) precipitates from the reaction mixture, e.g. on cooling, and can be separated, e.g. by filtration or centrifuging, if desired.

Basic hydrolysis may preferably be carried out by heating an aqueous solution of hydroxydes or carbonates of alkali metals or hydroxides of alkaline earth metals. One may preferably use an aqueous solution of sodium hydroxide, potassium hydroxide, sodium carbonate, potassium carbonate, calcium hydroxide, potassium hydrogen carbonate. Organic amines (e.g. triethyl amine) may also be used in the hydrolysis step.

Acidic hydrolysis may preferably be accomplished by using an aqueous mineral acid. One may preferably proceed by hydrolyzing a borate of the Formula IV by heating same with an aqueous solution of hydrochloric acid, hydrogen bromide, sulfuric acid or phosphoric acid. Hydrolysis may also be accomplished by using organic acids (e.g. acetic acid, propionic acid, etc.).

Hydrolysis of the compounds of the Formula IV may also be carried out in aqueous medium in the presence of a water-miscible organic solvent. For this purpose e.g. alcohols (e.g. methanol, ethanol), ketones (e.g. acetone), ethers (e.g. dioxane), acid amides (e.g. formamide, dimethyl formamide), sulfoxides (e.g. dimethyl sulfoxide), or pyridine may be used.

The quinoline-3-carboxylic acid of the Formula I thus obtained may be isolated e.g. by adjusting the pH value of the aqueous solution to a suitable value and separating the precipitated crystals e.g. by filtration or centrifuging or by lyophilization of the aqueous reaction mixture.

The compounds of the Formula I can be converted into pharmaceutically acceptable salts thereof by methods known per se. Thus preferably acid addition salts formed with hydrogen halides, sulfonic acids, sulfuric acid or organic acids. One may preferably form chlorides, bromides, 4-methyl-phenyl-sulfonates, methane sulfonates, maleates, fumarates, benzoates, etc. The compounds of the Formula I form salts with alkali or alkaline earth metals or other metal ions as well. Accordingly sodium, potassium, magnesium, silver, copper salts, etc. may be prepared.

The compounds of the general Formula I and pharmaceutically acceptable salts thereof can be converted into hydrates (e.g. hemihydrates, trihydrates, etc.) by methods known per se.

According to a further aspect of the present invention there are provided new compounds of the Formula IV (wherein R, $R^1$ and $R^2$ are as stated above).

The starting materials of the Formula II can be prepared e.g. by reacting 1-cyclopropyl-6-fluoro-7-chloro-4-oxo-1,4-dihydro-quinoline-3-carboxylic acid (German open application 3,141,854) with a boron derivative such as a compound of the Formula V

(V)

wherein $R^1$, $R^2$ and $R^5$ stand for halogen, for an aliphatic acyloxy group containing 2 to 6 carbon atoms optionally substituted by halogen, or for an aromatic acyloxy group containing 7 to 11 carbon atoms or with fluoroborate in an aqueous or an organic medium.

SPECIAL EXAMPLES

Further details or the present invention are to be found in the following Examples without limiting the scope of protection to the said Examples.

EXAMPLE 1

4.1 g of (1-cyclopropyl-6-fluoro-7-chloro-1,4-dihydro-4-oxo-quinoline-3-carboxylate-$O^3$,O)$^4$-bis(aceto-O)-boron and 2.8 g of piperazine anhydride are heated in 16 ml of dimethyl sulfoxide to 110° C. under stirring. 40 ml of a 3 $^w$/v % aqueous sodium hydroxide solution are added to the brownish-red solution and the reaction mixture is boiled under reflux for an hour. The hot pale-yellow solution is filtered and the pH value is adjusted to 7 by adding 1.8 ml of 96% acetic acid. The reaction mixture is cooled to room temperature, the precipitated white crystals are filtered, washed with water and methanol and dried. The crude product is purified by boiling in 10 ml water. Thus 2.99 g of 1-cyclopropyl-6-fluoro-7-(1-piperazinyl)-1,4-dihydro-4-oxo-quinoline-3-carboxylic acid are obtained. The product decomposes at 255° C.

Analysis for the Formula $C_{17}H_{18}FN_3O_3$: Calculated: C=61.62%; H=5.48%; N=12.68%. Found: C=61.58%; H=5.50%; N=12.61%.

EXAMPLE 2

By reacting (1-cyclopropyl-6-fluoro-4-chloro-1,4-dihydro-4-oxo-quinoline-3-carboxylate-$O^3$,$O^4$)-bis-(acetato-O)-boron and N-methyl-piperazine according to Example 1. 1-cyclopropyl-6-fluoro-7-(4-methyl-piperazino)-1,4-dihydro-4-oxo-quinoline-3-carboxylic acid is prepared. The product decomposes at 248°-250° C.

EXAMPLE 3

4.1 g of (1-cyclopropyl-6-fluoro-7-chloro-1,4-dihydro-4-oxo-quinoline-3-carboxylate-$O^3$,$O^4$)-bis(acetato-O)-boron and 3.7 g of N-ethyl-piperazine are heated in 16 ml of dimethyl sulfoxide to 90° C. under stirring. After 10 minutes 40 ml of a 3 $^w$/w % aqueous sodium hydroxide solution are added and the reaction mixture is boiled for an hour under reflux. The hot solution is filtered and the pH value is adjusted to 7 with 96% acetic acid. The reaction mixture is cooled, the precipitated crystals are filtered and washed with water. Thus 3.3 g of 1-cyclopropyl-7-(4-ethyl-piperazinyl)-6-fluoro-1,4-dihydro-4-oxo-quinoline-3-carboxylic acid are obtained. M.p.: 183°-185° C.

Analysis for the Formula $C_{19}H_{22}FN_3O_3$: Calculated: C=63.35; H=6.17; N=11.69. Found: C=63.31; H=6.21; N=11.70.

EXAMPLE 4

3.3 g of (1-cyclopropyl-6-fluoro-7-chloro-1,4-dihydro-4-oxo-quinoline-3-carboxylate-$O^3$,$O^4$)-difluoro-boron are reacted with 3.7 g of N-ethyl-piperazine according to Example 3. Thus 3.4 g of 1-cyclopropyl-7-(4-ethyl-1-piperazinyl)-6-fluoro-1,4-dihydro-4-oxo-quinoline-3-carboxylic acid are obtained which in admixture at any ratio with the product of Example 3 no depression of the melting point occurs.

What we claim is:

1. A compound of the Formula IV

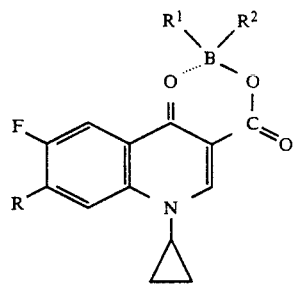

wherein R stands for piperazinyl, 4-methyl-piperazinyl or 4-ethyl-piperazinyl group, $R^1$ and $R^2$ stand for halogen, for an aliphatic acyloxy group having 2 to 6 carbon atoms optionally substituted by halogen, or for an aromatic acyloxy group having 7 to 11 carbon atoms.

2. The compound of the Formula (IV) defined in claim 1 wherein $R^1$ and $R^2$ are each acetyloxy.

3. The compound of the Formula (IV) defined in claim 1 wherein $R^1$ and $R^2$ are each fluoro.

* * * * *